– - -

United States Patent [19]

Wong

[11] Patent Number: 4,496,554

[45] Date of Patent: Jan. 29, 1985

[54] OLEAGINOUS EMOLLIENT VEHICLE FOR STEROID FORMULATIONS

[75] Inventor: Thomas M. Wong, North Brunswick, N.J.

[73] Assignee: E. R. Squibb & Sons, Inc., Princeton, N.J.

[21] Appl. No.: 311,495

[22] Filed: Oct. 15, 1981

Related U.S. Application Data

[63] Continuation of Ser. No. 4,100, Jan. 17, 1979, abandoned.

[51] Int. Cl.$^3$ .............................................. A61K 31/56
[52] U.S. Cl. ..................................... 514/179; 514/177
[58] Field of Search ......................................... 424/238

[56] References Cited

U.S. PATENT DOCUMENTS

| 2,845,381 | 7/1958 | Tindall | 424/238 |
|---|---|---|---|
| 2,942,008 | 6/1960 | Lubowe | 424/236 |
| 3,183,158 | 5/1965 | Brückner | 424/238 |
| 3,592,930 | 7/1971 | Katz et al. | 424/358 |
| 3,924,004 | 12/1975 | Chang et al. | 424/238 |

FOREIGN PATENT DOCUMENTS 1195943 6/1970 United Kingdom ................ 424/238

OTHER PUBLICATIONS

Chem. Abst. 80, 19396(g) (1974)–Nishihara.
The Merck Index, 9th ed., notes 1846 and 4445 (1976).

*Primary Examiner*—Douglas W. Robinson
*Attorney, Agent, or Firm*—Lawrence S. Levinson; Donald J. Barrack

[57] ABSTRACT

An ointment-like composition for the topical administration of a corticosteroid is disclosed.

For the topical administration of corticosteroids an ointment-like composition comprising not less than 40% by weight of isostearyl alcohol can be used.

9 Claims, No Drawings

OLEAGINOUS EMOLLIENT VEHICLE FOR STEROID FORMULATIONS

This is a continuation of application Ser. No. 4,100, filed Jan. 17, 1979, and now abandoned.

BACKGROUND OF THE INVENTION

Corticosteroids have been used for the treatment of various dermatoses when applied topically. The steroids have been formulated as creams, ointments, lotions and aerosol sprays. Of the various formulations, ointments have in the past received the least patient acceptance. Ointments do, however, have the beneficial therapeutic affect of occlusiveness, a highly desirable characteristic for topical steroid therapy.

Early ointment formulations used in topical steroid therapy were based largely on fats, grease and petrolatum. Early synthetic bases for use in ointments are described in U.S. Pat. Nos. 2,627,938 and 2,628,187 which describe a petroleum oil vehicle which has been thickened with polyethylene. Although these vehicles have gained wide acceptance in the steroid field they do have serious disadvantages. Cosmetically they are not as elegant as patients would like. More specifically, they impart a lingering greasy feeling to the skin, which is most noticeable on hairy skin. These ointment bases are also water insoluble and, therefore, difficult to wash off the skin. Still further, oil bases of the past are prone to stain garments and bedding with which they come in contact.

Aside from the cosmetic problems enumerated above, ointment bases posses serious physical stability problems when petroleum vehicles are employed. Excessive temperatures can cause softening or melting of the vehicle and result in the separation of suspended components. This separation of suspended components (breaking down of the gel structure is a serious problem because uniform distribution of the active steroid ingredient is considered important for successful topical corticosteroid treatment. The steroids are not soluble in petrolatum vehicles and, therefore, a steroid suspension is the only choice for incorporation of the steroid into a petrolatum vehicle.

More recently, Carbowax, a mixture of polyethylene glycol polymers has been used as an ointment-like base. These compositions have the advantage of being water-washable, but they are still greasy and cosmetically inelegant. Furthermore, Carbowax vehicles are not occlusive.

U.S. Pat. No. 3,592,930 issued July 13, 1971, discloses an ointment-like vehicle which is said to be water-washable and occlusive and which comprises as its essential ingredients a fatty alcohol having 16 to 24 carbon atoms and a glycol. The glycol solvent is said to function as a solvent for a glycol-soluble drug or as a carrier for a glycol-insoluble drug. The fatty alcohol component is said to be "a solid component which naturally thickens the composition".

U.S. Pat. No. 3,924,004 discloses a formulation comprising a saturated fatty alcohol having from 16 to 24 carbon atoms, propylene carbonate, and a glycol solvent.

SUMMARY OF THE INVENTION

It is an object of this invention to provide an oleaginous emollient vehicle for steroid formulations.

It is a further object of this invention to provide an ointment-like vehicle which eliminates the feeling of greasiness when applied to the skin without scarificing the occlusive property of an ointment.

It is a further object of this invention to provide an ointment-like vehicle which is not affected by temperature extremes. More specifically, it is an object of this invention to provide a steroid vehicle which at temperatures up to 50° C. does not show evidence of bleeding or syneresis, and which can be extruded from tubes at refrigerator temperatures without difficulty.

It is an object of this invention to provide an ointment-like vehicle for steroid formulations which has enhanced emolliency and improved occlusive properties.

It is an object of this invention to provide an ointment-like steroid vehicle which does not stain clothing or bedding with which it comes in contact.

It is an object of this invention to provide a vehicle for steroid formulations which will provide for uniform distribution of the steroid and enhance therapeutic efficacy.

These and other objects which will be apparent to the practitioner of this invention can be achieved by utilizing isostearyl alcohol in place of vegetable oil or petroleum hydrocarbons in an ointment-like vehicle. More specifically, the isostearyl alcohol should make up at least 40% by weight of the steroid formulation.

DETAILED DESCRIPTION OF THE INVENTION

In its broadest aspect, the invention comprises the use of at least 40% weight of isostearyl alcohol in a steroid formulation. The isostearyl alcohol will serve both as a principal solvent for the formulation and as an emollient. The fatty alcohols used in the prior art have been the lower molecular weight fatty alcohols in minor amounts or, when larger amounts of fatty alcohol have been used, the higher molecular weight solid fatty alcohols. While the lower molecular weight fatty alcohols are fluids they are undesirable because of their odor and because of their tendency to irritate the skin. Isostearyl alcohol on the other hand is a non-irritating liquid which does not have as strong an odor as its lower molecular weight homologs.

In a preferred embodiment of this invention the steroid formulation will also contain 5–12% by weight of a high melting point wax (melting point range 60°–90° C.), e.g., carnauba wax, candellia wax, ozokerite wax, and beeswax, and 4–10% by weight of a moderately high melting polyhydric alcohol ester of a fatty acid (melting point range 60°–90° C.), e.g., propylene glycol distearate and ethylene glycol distearate. The wax and the polyhydric alcohol ester of a fatty acid together form a network (or matrix) within which is contained the steroid partially dissolved in the isostearyl alcohol. The formulation can also contain a simple fatty acid ester which functions as a non-greasy emollient. The emollient will disappear when rubbed into the skin and lends lubricity to the skin. Exemplary of the simple fatty acid esters contemplated are isopropyl myristate and isopropyl palmitate.

Cosolvents may also be used along with the isostearyl alcohol. Particularly preferred as a cosolvent is propylene carbonate, which may be used in an amount from about 1% to 7% by weight of the formulation. When using a cosolvent it may be advantageous to include in the formulation a coupler. The term "coupler" is used to describe a compound which insures the miscibility of the solvents. When propylene carbonate is used as a cosolvent with isostearyl alcohol, polyoxypropylene stearyl ether serves as an effective coupler.

To enhance the occlusive property of the ointment-like vehicle a polysiloxane such as dimethylpolysiloxane liquid may be employed in an amount of about 5% to 10% by weight of the formulation.

The ointment-like steroid vehicle described herein can also contain various additional ingredients which are conventional in the pharmaceutical art. These additional ingredients can be used to improve the stability, homogeneity, consistency, emolliency, penetrability and the cosmetic elegance of the vehicle. The choice of particular ingredients is within the level of ordinary skill in the art and the practitioner of this invention will choose the various adjuvants depending on the particular qualities he wishes the vehicle to have. For example, the art recognizes the equivalence of 1,3-butylene glycol and a simple fatty acid ester in an ointment formulation. The 1,3-butylene glycol can be used in place of all, or part, of the simple fatty acid ester as a non-greasy emollient.

A method for preparing the preferred steroid formulations of this invention comprises first dissolving the steroid drug in the cosolvent. To a separate container, preferably a steam jacketed stainless steel vessel equipped with a stirrer, is added the rest of the ingredients with the exception of the polysiloxane. These are melted together and stirred until a clear melt is effected. To this solution is added the steroid dissolved in the cosolvent and the resulting solution is stirred and heated. The mixture is next shock-cooled and the resultant formulation is then placed in a planetary type mixer to which is added the polysiloxane ingredient. To improve the quality of the finished product, the resultant formulated mixture may be passed through a roller mill.

Alternately, the above-described procedure can be modified by including high shearing equipment in the steam jacketed stainless steel vessel. Immediately prior to shock-cooling, the mixture of ingredients can be subjected to high shear. In this method, the polysiloxane ingredient can be added prior to the high shear mixing.

The vehicle described herein is suitable for use with topical antiinflammatory steroids. Exemplary of the steroids contemplated are the acetonide derivatives of steroids of the pregnane series described in U.S. Pat. No. 3,048,581. Included within the steroids described by this patent are triamcinolone acetonide and halcinonide. It is emphasized that these steroids are meant to be exemplary only and it is not meant to limit this invention to use with any particular steroid or group of topically active antiinflammatory steroids. The steroids incorporated in the formulation of this invention may be present in an amount of from about 0.01% by weight to about 1.0% by weight, preferably from about 0.025% by weight to about 0.5% by weight.

The following examples are specific embodiments of this invention.

EXAMPLE

The various ingredients set forth below are formulated into oleaginous emollient vehicles for steroid formulations. Alternative methods of formulation are set forth below.

Method I

The carnauba wax and ethylene glycol distearate are mixed with isopropyl myristate (formulations 1–7) or 1,3-butylene glycol (formulations 8–14), polyoxypropylene stearyl ether and isostearyl alcohol. While stirring, the mixture is heated until the wax melts and the temperature is maintained at 80°–85° C. for a few minutes. In a separate container, the halcinonide is dissolved in propylene carbonate with the aid of heat. The halcinonide solution is combined with the wax mixture and the temperature of the mixture is brought to 80°–85° C. The molten mixture is transferred to a shock cooling machine and quickly cooled using water maintained in the 20°–30° C. range. The emollient base obtained is gently heated to 35° C. and combined with Corning DC 200 fluid (also heated to 35° C.) in a planetary mixer. The emollient is then passed through a roller mill.

Method II

The carnauba wax and ethylene glycol distearate are mixed with isopropyl myristate (formulation 1–7) or 1,3l-butylene glycol (formulations 8–14), polyoxypropylene stearyl ether and isostearyl alcohol. While stirring the mixture is heated until the wax melts and the temperature is maintained at 80°–85° C. for a few minutes. In a separate container, the halcinonide is dissolved in propylene carbonate with the aid of heat. The halcinonide solution is combined with the molten wax mixture and the Corning DC 200 Fluid is then added. The temperature of the mixture is raised to 80°–85° C. and the mixture is subjected to high shear stirring which is maintained until just prior to transfer to a shock cooling machine for immediate quick cooling using water maintained in the 20°–30° range.

| Ingredient | Quantities (% by weight.) | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Halcinonide | 0.1 | 0.1 | 0.1 | 0.1 | 0.1 | 0.1 | 0.1 | 0.1 | 0.1 | 0.1 | 0.1 | 0.1 | 0.1 | 0.1 |
| Carnauba Wax | 9 | 9 | 9 | 9 | 9 | 9 | 9 | 9 | 9 | 9 | 9 | 9 | 9 | 9 |
| Ethylene Glycol Distearate | 7 | 7 | 7 | 7 | 7 | 7 | 7 | 7 | 7 | 7 | 7 | 7 | 7 | 7 |
| Isopropyl Myristate | 20 | 20 | 20 | 20 | 20 | 20 | 20 | — | — | — | — | — | — | — |
| 1,3-Butylene Glycol | — | — | — | — | — | — | — | 15 | 15 | 15 | 15 | 15 | 15 | 15 |
| Polyoxypropylene Stearyl Ether | 5 | 5 | 5 | 5 | 5 | 5 | 5 | 5 | 5 | 5 | 5 | 5 | 5 | 5 |
| Propylene Carbonate | 1 | 2 | 3 | 4 | 5 | 6 | 7 | 1 | 2 | 3 | 4 | 5 | 6 | 7 |
| Corning DC 200 | 10 | 10 | 10 | 10 | 10 | 10 | 10 | 10 | 10 | 10 | 10 | 10 | 10 | 10 |
| Isostearyl Alcohol | 47.9 | 46.9 | 45.9 | 44.9 | 43.9 | 42.9 | 41.9 | 52.9 | 51.9 | 50.9 | 49.9 | 48.9 | 47.9 | 46.9 |

What is claimed is:

1. A composition for the topical administration of an antiinflammatory corticosteroid comprising an effective amount of the corticosteroid and not less than 40% by weight of the composition of isostearyl alcohol.

2. A composition in accordance with claim 1 further comprising a wax having a melting point of 60°–90° C. and a polyhydric alcohol ester of a fatty acid.

3. A composition in accordance with claim 2 wherein the wax is carnauba wax and the fatty acid ester is ethylene glycol distearate.

4. A composition in accordance with claim 1 further comprising an additional solvent.

5. A composition in accordance with claim 4 wherein the additional solvent is propylene carbonate.

6. A composition in accordance with claim 1 wherein the corticosteroid is present in an amount of from about 0.01% by weight to about 1.0% by weight.

7. A composition in accordance with claim 6 wherein the corticosteroid is present in an amount of from about 0.025% by weight to about 0.5% by weight.

8. A composition in accordance with claim 1 comprising about 0.01% weight to about 1.0% by weight of a corticosteroid, 5% by weight to 12% by weight of a wax having a melting point of 60° to 90° C., and 4% by weight to 10% by weight of a polyhydric alcohol ester of a fatty acid.

9. A composition in accordance with claim 8 further comprising about 1% by weight to 7% by weight propylene carbonate.

* * * * *